United States Patent [19]

Miller et al.

[11] Patent Number: 4,481,471

[45] Date of Patent: Nov. 6, 1984

[54] METHOD AND APPARATUS FOR THE DETECTION OF ANOMALIES IN ROTATING MEMBERS

[75] Inventors: Robert C. Miller, Penn Hills; Walter J. Carr, Jr., Wilkins, both of Pa.

[73] Assignee: Westinghouse Electric Corp., Pittsburgh, Pa.

[21] Appl. No.: 292,973

[22] Filed: Aug. 14, 1981

[51] Int. Cl.³ ............................................. G01N 27/82
[52] U.S. Cl. ..................................................... 324/240
[58] Field of Search ............................. 324/226–243, 324/220, 179, 174, 262

[56] References Cited

U.S. PATENT DOCUMENTS

| | | | |
|---|---|---|---|
| 2,650,344 | 8/1953 | Lloyd | 324/260 X |
| 2,980,850 | 4/1961 | Cochran | 324/242 |
| 3,494,459 | 5/1969 | Prindle et al. | 324/242 |
| 3,579,099 | 5/1971 | Kanbayashi | 324/235 |
| 3,612,987 | 10/1971 | Placke et al. | 324/242 |
| 3,906,357 | 9/1975 | Runshang | 324/226 |
| 3,944,911 | 3/1976 | Törnblom | 324/242 |
| 4,146,837 | 3/1979 | Bashkirov | 324/238 |
| 4,352,065 | 9/1982 | Rogachev et al. | 324/240 |

*Primary Examiner*—Gerard R. Strecker
*Assistant Examiner*—Warren S. Edmonds
*Attorney, Agent, or Firm*—D. Schron

[57] ABSTRACT

A detector operable to detect cracks in a rotating member generates an alternating eddy current in the rotating member with an external coil surrounding the rotating member. A pick-up coil senses changes in the magnetic field of the eddy current due to a crack. The frequency of the excitation current is very much lower than the frequency of rotation of the rotating member and a plurality of samples are taken for each degree location. The output signal of the pick-up coil is comprised of both the crack indicative component and a residual or induced magnetism component. The signal is processed so as to extract the desired crack indicative component.

20 Claims, 27 Drawing Figures

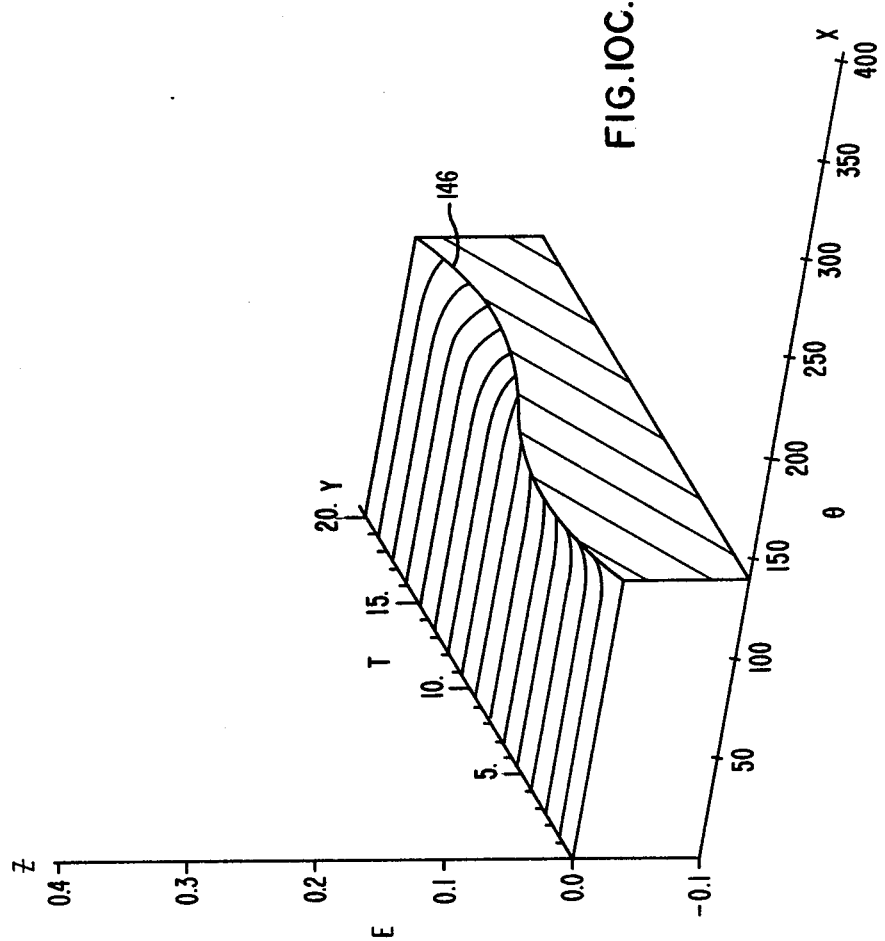

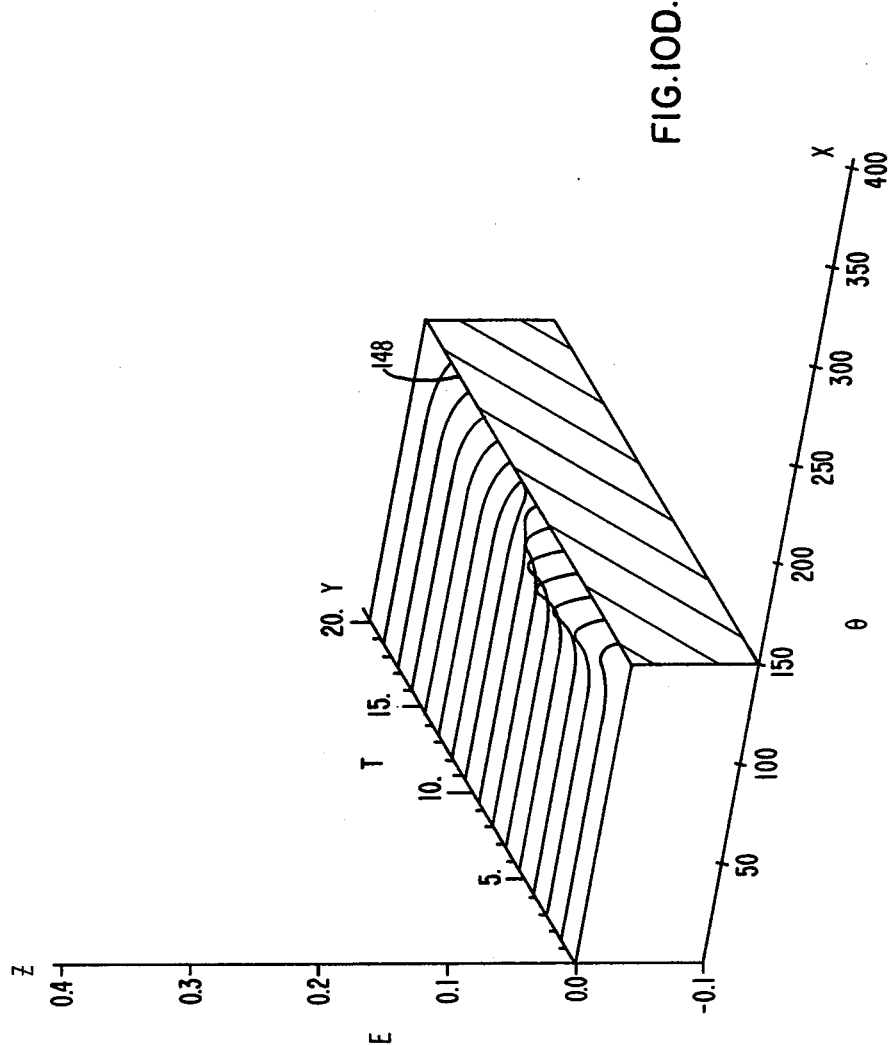

_4,481,471_

METHOD AND APPARATUS FOR THE DETECTION OF ANOMALIES IN ROTATING MEMBERS

BACKGROUND OF THE INVENTION

1. Field of the Invention

The invention in general relates to flaw detection, and more particularly to flaw detection using the eddy current principle.

2. Description of the Prior Art

If a current carrying coil is brought near a metallic member, localized eddy currents are produced in the member. If a pick-up or sensing coil is placed adjacent the member in the vicinity of the eddy currents a corresponding voltage will be produced by the pick-up coil indicative of these currents. This principle is utilized in a technique to detect surface cracks and shallow defects in the metal object since the pick-up coil will produce a first signal in the absence of any flaws and a second and different signal in the presence of these flaws.

The coil arrangement is mechanically scanned over the member while it is off-line and by recording the pick-up coil's output signal, as well as the location of the coil arrangement relative to the member under test, an indication may be obtained of the presence and location of any flaws.

With such an arrangement, because of skin effects, the depth at which flaws may be detected is a function of the frequency of the excitation current. For example, to detect a crack in a typical steel member one inch (2.54 cm) from the surface would require an excitation current frequency of approximately 1 Hertz (Hz). The detection of a signal at this low frequency is relatively difficult and accordingly, frequencies in the order of 60 Hz and higher are generally used with such apparatus. 60 Hz, however, corresponds to a maximum detection depth of approximately ⅛ inch (0.317 cm) which may be detected with facility and hence, cracks at depths below this value may go undetected.

The present invention utilizes eddy current techniques for the detection of defects in rotating members in an arrangement which can detect cracks (or other anomalies) at depths exceeding those detectable with equal facility by the mechanically scanned off-line arrangement.

SUMMARY OF THE INVENTION

Apparatus for detecting anomalies in an electrically conductive rotating member in accordance with the present invention includes a current conducting means such as a coil contiguous to the rotating member and operable to establish a circumferential alternating eddy current in the rotating member as the member rotates. This alternating eddy current also establishes a corresponding external magnetic field. An excitation circuit provides the coil with an AC excitation current having a certain frequency f. A sensing means such as a pick-up coil fixed in space relative to the moving member is positioned for detecting any changes in the external magnetic field caused by the anomalies. The voltage produced by the magnetic field anomaly is mainly due to the relative motion. The coil provides an output signal which is processed by a signal processing circuit in a manner so as to provide an output indication of anomaly location within the rotating member.

The frequency f is much lower than the frequency of rotation of the rotating member and a number of samples of the pick-up coil's output signal is obtained during the period of a cycle for each predetermined angular location of the rotating member. For example, a certain imaginary point on the surface of the rotating member, corresponding to some degree location, $\theta i$, will pass the pick-up coil repeatedly in the time that it takes for the excitation current to experience one cycle. Each time the $i^{th}$ degree location passes the pick-up coil, a sample of its output voltage is taken so that hundreds of samples can be accumulated for that particular degree location in one period of the excitation current. The output signal of the pick-up coil includes not only a crack anomaly indicative component but also a permanent moment or residual magnetic component, which is unwanted since it is not necessarily related to crack anomalies. The signal processing circuitry is operable to extract just the desired component of the combined signal in a fashion which substantially reduces any noise components.

BRIEF DESCRIPTION OF THE DRAWINGS

FIGS. 10A through 10E are waveforms illustrating the operation of the circuitry of FIG. 8;

DESCRIPTION OF THE PREFERRED EMBODIMENT

Figure 1A:
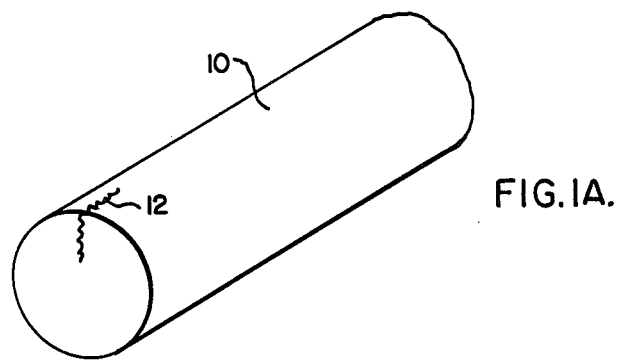
FIGS. 1A through 1C illustrate various cracks in several rotating members.
Figure 1B:
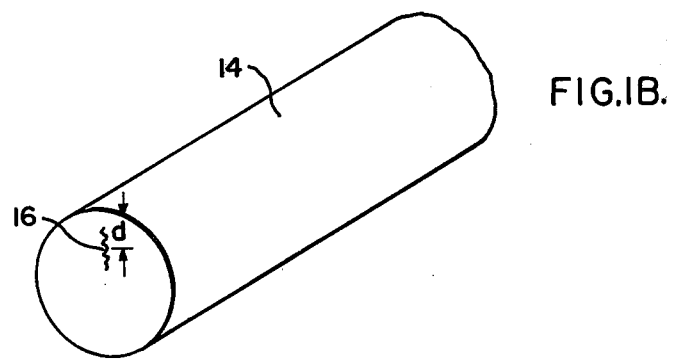

Referring now to FIG. 1A there is shown a section of a shaft 10 which includes a surface crack 12. Normally, when the apparatus to which the shaft is connected is shut down and the shaft is in a non-rotating condition, the surface of the shaft 10 would be scanned by the prior art coil arrangement previously described and the presence of crack 12 would be detected thereby. In FIG. 1B a shaft 14 is illustrated with an internal crack 16 at a distance d (measured to the center of the crack)

from the surface. Depending upon the distance d, crack 16 may or may not be detected by the scanning coil arrangement of the prior art.

Figure 1C:
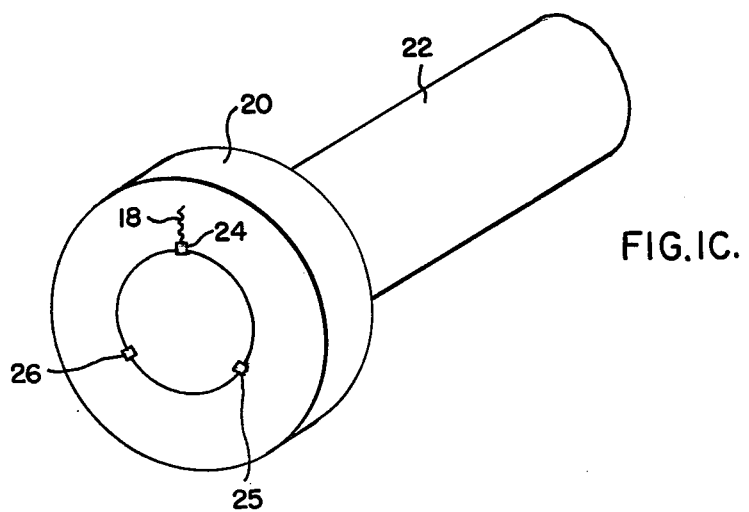

A similar problem exists with the detection of crack 18 in the arrangement of FIG. 1C which illustrates a disc member 20 which may be an integral part of, or fitted onto a shaft 22. When fitted onto the shaft, the disc member 20 is keyed to the shaft 22 such as illustrated at 24, 25 and 26. During on line operation of the arrangement of FIG. 1C wherein the shaft and disc member are rotating, stress cracks may occur in the vicinity of the keys (as well as other locations) which if not detected can lead to undesired consequences. With the present invention not only can these deep cracks be detected, but they can be detected, along with surface cracks, while the apparatus is on-line and rotating.

Figure 2:
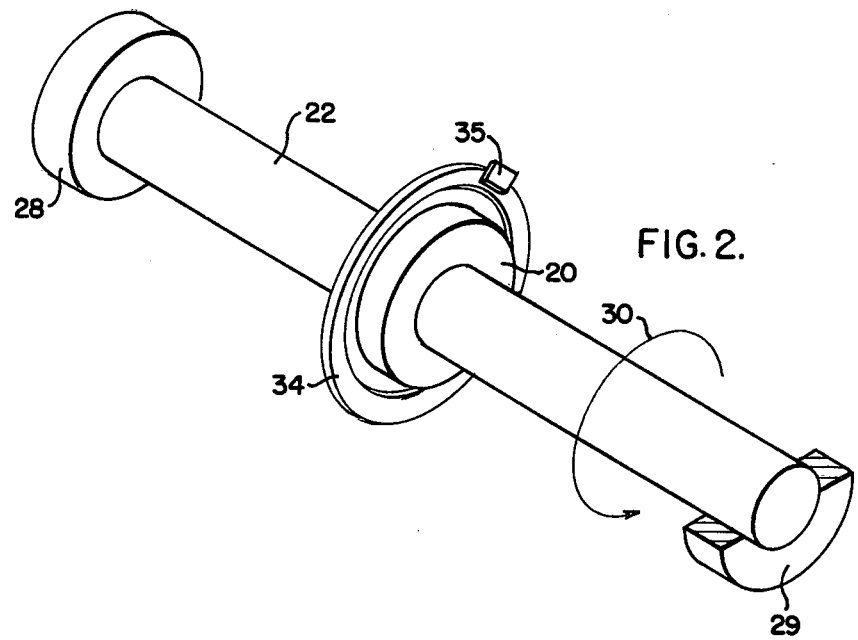
FIG. 2 illustrates the placement of coils relative to a rotating member, in accordance with an embodiment of the present invention.

An embodiment of the present invention is illustrated in FIG. 2 which shows the disc member 20 and shaft 22, the latter being positioned in bearings 28 and 29, with the on-line rotation of the shaft being indicated by the arrow 30. The invention includes a magnetizing or excitation coil 34 contiguous to the rotating member so as to establish a circumferential eddy current therein as it rotates. A fixed sensing or pick-up coil 35 is positioned adjacent to the excitation coil 34 and in proximity to the rotating member in which the eddy current is induced. An axial section through the disc and shaft members together with the placement of the coils is further illustrated in FIGS. 3A and 3B.

As will be explained, and with reference to FIG. 3A, an extremely low frequency excitation signal, for example a fraction of a Hz, is applied to leads 38, 39 of excitation coil 34 so as to establish a circumferential eddy current in the rotating member. The eddy current distribution is as indicated by the circumferential arrows 40 and an average eddy current beneath the pick-up coil 35 is as indicated by the heavy arrow 42. The frequency of the excitation current will depend on various factors such as the material in which the eddy current is induced, and the maximum depth to which cracks are to be detected. By way of example, for a steel member 20 rotating at 1800 rpm the excitation signal applied to the excitation coil 34 may be in the order of 1/20 Hz, such signal having a period T=20 seconds.

The eddy current illustrated is at a particular instant of time in the period of the excitation current. That is, the eddy current will not only vary in magnitude but will also vary in direction during rotation of the member. By way of example for an exciting current frequency of 1/20 Hz and for an 1800 rpm member, the member will rotate 600 times in the time it takes for the exciting current to complete one cycle.

Figure 3A:
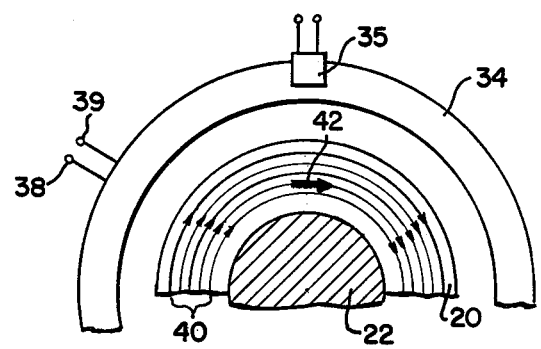
FIGS. 3A and 3B illustrate the generation of an eddy current in a rotating member and the effect of the crack on the eddy current.
Figure 3B:
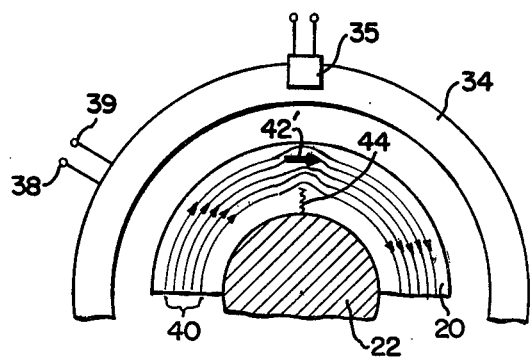

FIG. 3B illustrates the arrangement of FIG. 3A, however with a crack 44 in the disc member 20. Since the eddy current cannot pass through the crack, the distribution will be around it thus bringing the average eddy current, as represented by heavy arrow 42', closer to the pick-up coil 35 when crack 44 passes beneath it.

The eddy current produces a magnetic field outside of the disc member and the perturbation of the eddy current due to the crack produces a change in the magnetic field such that the pick-up coil produces an output signal indicative of the change. This concept is further illustrated in FIGS. 4A to 4C.

Figure 4A:
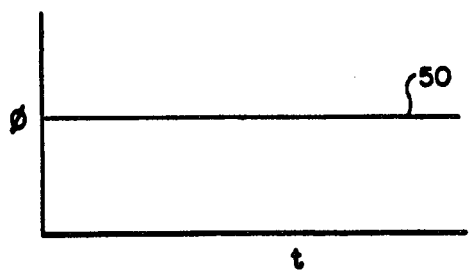
FIGS. 4A through 4C are curves illustrating certain signals present in the arrangement of FIGS. 3A and 3B.

In FIG. 4A magnetic field in terms of flux $\phi$ is plotted on the vertical scale while time is plotted on the horizontal scale. Curve 50 of FIG. 4A represents the situation of FIG. 3A wherein the eddy current distribution remains unchanged so as to produce an essentially constant flux at the pick-up coil 35 over the rotational period of time.

Figure 4B:
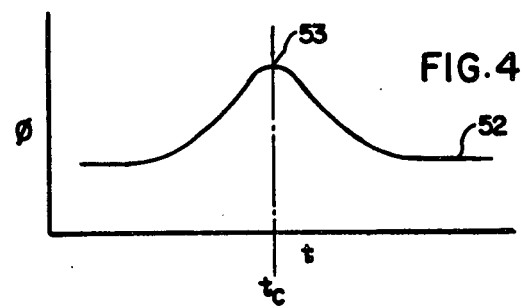

With the presence of a crack, as illustrated in FIG. 3B, the perturbation of the average eddy current causes the flux at the pick-up coil 35 to increase from its quiescent value to some maximum value as the crack passes beneath the pick-up coil and thereafter to reduce back to its quiescent value. This situation is illustrated in FIG. 4B by the curve 52 which reaches a peak 53 at a time $t_C$ corresponding to the time when the crack 44 passes under the pick-up coil.

Figure 4C:
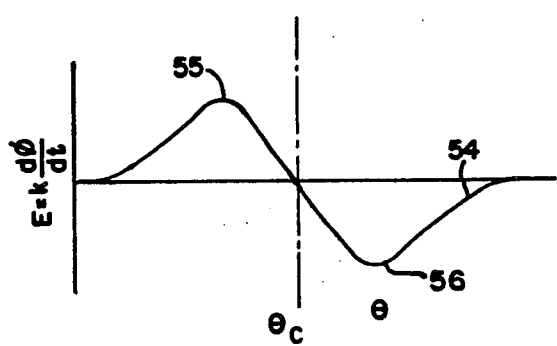

The voltage E produced by the pick-up coil 35 in response to this flux change is illustrated in FIG. 4C. The voltage produced by the pick-up coil 35 is proportional to the rate of change of flux with time, and this quantity $E = k d\phi/dt$ is plotted on the vertical axis. The angular position $\theta$ of the rotating member is plotted on the horizontal axis. Curve 54 illustrates the resulting pick up coil output signal in response to the flux change 53 of FIG. 4B. In response to this flux change it is seen that curve 54 reaches a positive peak 55, passes through a zero value at an angular position $\theta_C$, corresponding to time $t_C$ when the flux reaches a peak value, and thereafter decreases to a negative peak value 56 after which the curve trails off and reduces to a zero value once again.

In summary therefore, FIG. 4A represents the steady state flux condition at the pick-up coil 35 in the absence of any cracks, and as illustrated by the situation of FIG. 3A. FIG. 4B represents the change in flux at the pick-up coil due to the crack 44 as illustrated in FIG. 3B and the rate of change of this flux results in an output signal from the pick-up coil, as illustrated in FIG. 4C.

Figure 5:
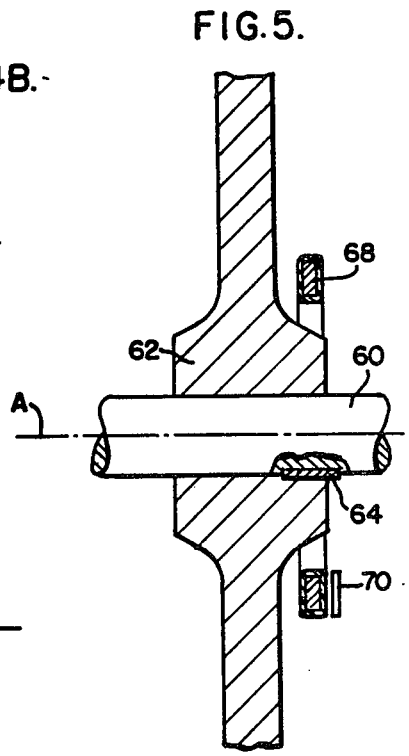
FIG. 5 illustrates the placement of the coils relative to a turbine disc.

This principle is utilized in the present invention, an embodiment of which will be described in connection with an arrangement for detecting cracks in a rotating member such as illustrated in FIG. 5.

FIG. 5 illustrates a portion of a turbine shaft 60 rotatable about an axis A, and to which is attached a turbine disc 62 keyed to the shaft 60 at various locations such as by key 64. One or more rows of turbine blades (not shown) would be attached to the disc 62. In order to detect any cracks, and particularly in the vicinity of the key 64, an excitation coil 68 is positioned near the base of the disc, in conjunction with a pick-up coil 70.

Figure 6:
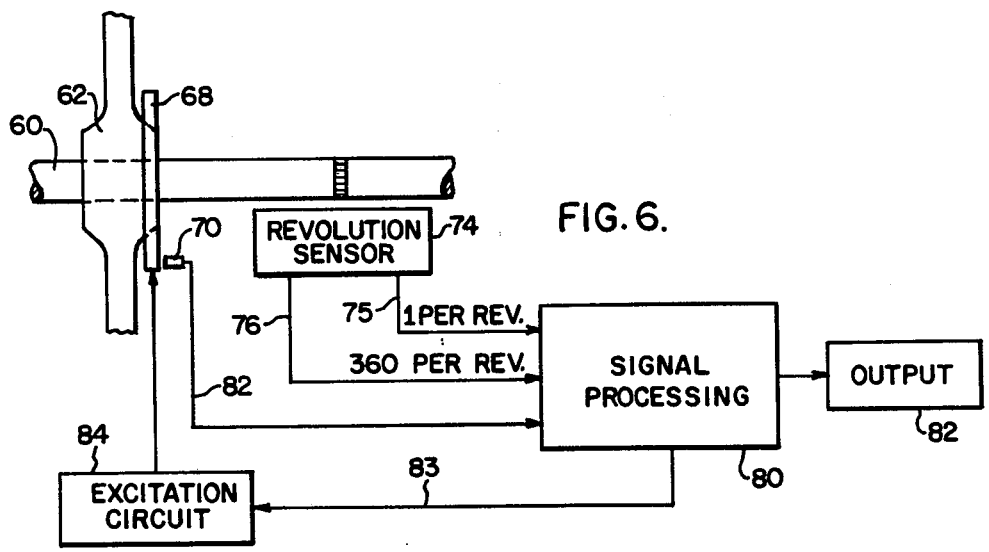
FIG. 6 is a block diagram illustrating an embodiment of the present invention.

FIG. 6 illustrates the rotating member of FIG. 5 together with other apparatus for crack determination in accordance with the teachings of the present invention. A revolution counter or sensor 74 is operable in a well-known manner to provide on line 75 an output signal for every complete revolution of shaft 60, and on line 76 an output signal for every degree of revolution so that 360 output signals are provided on line 76 to every one output signal provided on line 75.

The revolution indications are provided to signal processing circuitry 80 which in conjunction with the output signal on line 82, from pick-up coil 70 is operable to determine the presence, angular location, and approximate size and depth of any cracks in the disc member. Signal processing circuitry 80 then provides this information to an output circuit 82 for recording and/or presentation to an operator. Signal processing circuitry 80 may also be operable to govern, via line 83, the excitation circuit 84 which is operable to provide the excitation coil 68 with a suitable excitation current.

Figure 7A:
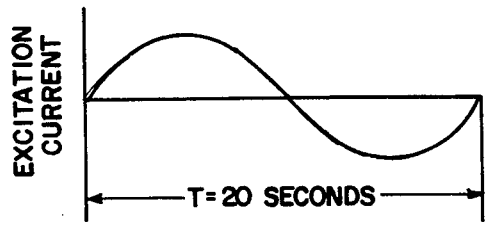
FIGS. 7A through 7C are waveforms illustrating certain timing relationships.
Figure 7B:
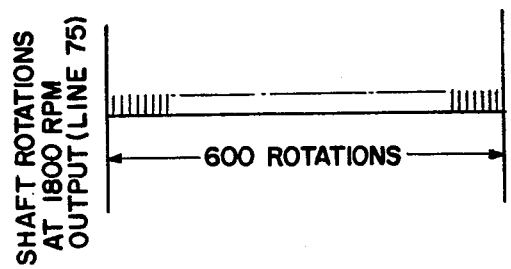
Figure 7C:
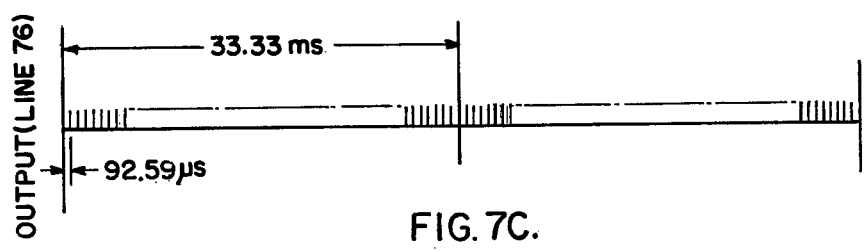

FIGS. 7A through 7C serve to illustrate the time relationship between the period of the excitation current and the rotation of the shaft member. In the example under consideration, the excitation current frequency is given as 1/20 Hz and the shaft rotational frequency is 1800 rpm. FIG. 7A illustrates one cycle of the excitation current which has a period T of 20 seconds ($T=1/f$). FIG. 7B illustrates the output signals appearing on line 75 and for the given rotational speed, there will be 600 rotations, and accordingly 600 output pulses during each 20-second period exciting current. The time between adjacent pulses in FIG. 7B is equivalent to 33.33 milliseconds during which period of time, output line 76 will provide 360 pulses as illustrated in FIG. 7C, wherein each pulse represents one degree of rotation, with the time between pulses being equivalent to 92.59 microseconds.

In one embodiment the effect of each degree location on the pick-up coil, for example starting with the 0° location, may be examined for a complete period of the excitation current before proceeding with an examination of the effect of the subsequent degree location. In the example given therefore, the effect of the 0° location will be examined 600 times before the effect of the 1° location is examined, also 600 times, with the process continuing until the effect of all 360° locations on the pick-up coil have been determined.

In a real-world situation the rotating shaft and disc which are of a steel construction, will have permanent magnetic moments distributed throughout the structure so as to cause the pick-up coil to provide a corresponding output due to these magnetic moments. The output signal of the pick-up coil during rotation of the disc will include, in addition to an unwanted noise component, an unwanted component due to the magnetic moments as well as a desired component due to a crack. The signal processing circuitry 80 (FIG. 6) is operable, in response to the pick-up coil output signal and rotational signals to substantially reduce the effects of the unwanted components and provide a high signal to noise ratio output signal indicative of a crack or other anomaly (if present).

Figure 8:
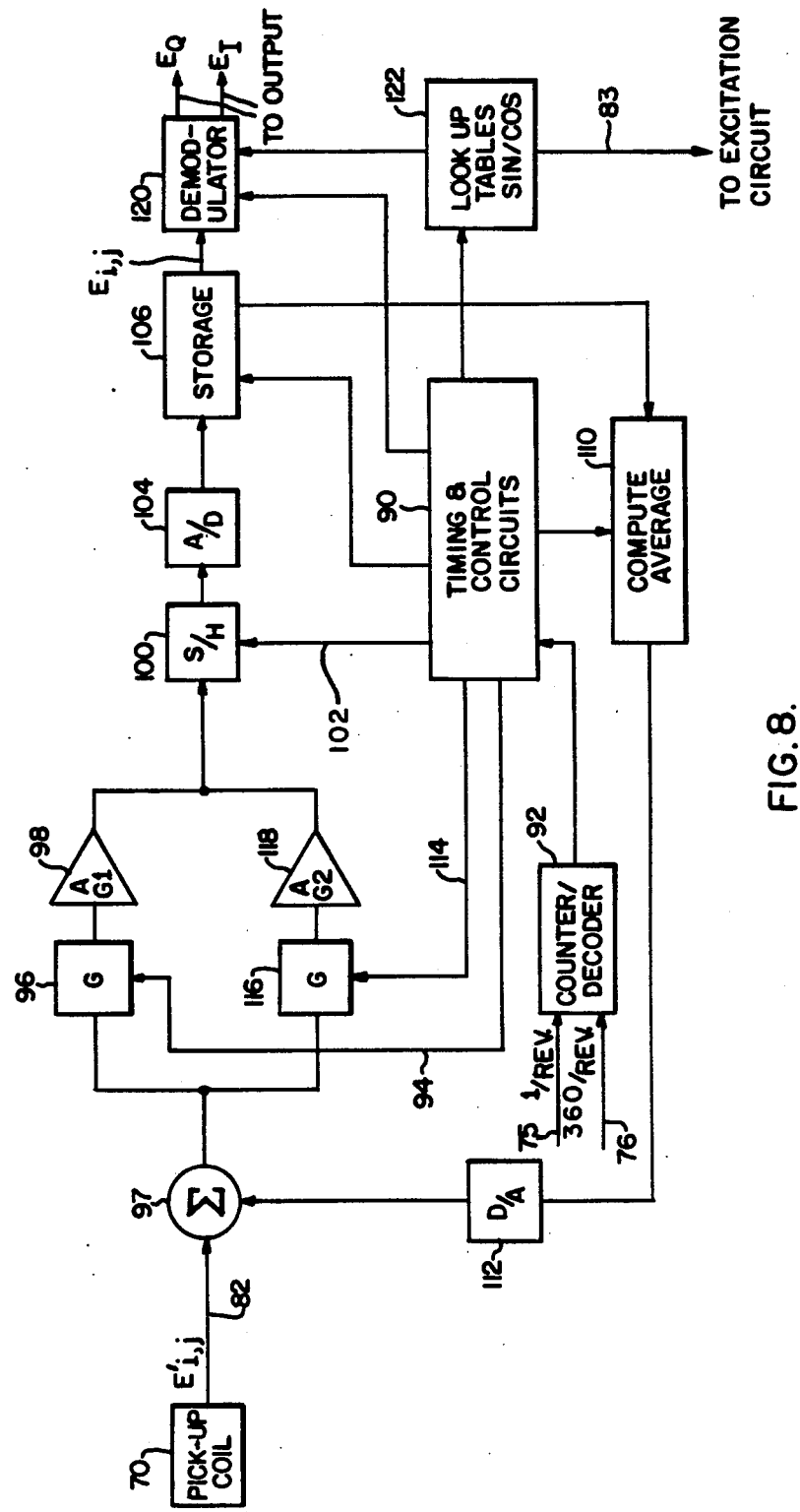
FIG. 8 is a block diagram showing the signal processing circuitry of FIG. 6 in more detail.

FIG. 8 illustrates in somewhat more detail one embodiment of signal processing circuit 80. Basically, the signal processing circuitry functions to examine for each degree location, the output signal of the pick-up coil 70, (which signal includes the permanent moment as well as the crack indicative components) and to compute an average for this signal over 600 samples. The pick-up coil output signal is thereafter examined for the same degree location a second time, however, the output signal is now subtracted from the previously computed average, resulting in an output signal for that particular degree location which substantially reduces the permanent magnetic moments signal. This output signal, as will be explained, is further processed to reduce noise and to provide first and second output signals indicative of both conductivity and permeability for each degree location.

Functionally, the signal processing circuitry 80 is governed by a timing and control circuit 90 which provides certain timing and control signals in response to the angular position of the shaft and disc as evidenced by the output of the counter/decoder circuit 92 which provides such indication in response to the input signals on lines 75 and 76.

When the output signal of the pick-up coil 70 is initially sampled the timing and control circuit 90 provides an enabling signal on line 94 to gate 96 so as to enable it. At this point summation circuit 97 is receiving and passing only the signal on line 82 from the pick-up coil 70. With the gating circuit 96 thus enabled, the amplifier 98 which has a relatively low gain is operable to amplify the signal which is then sampled each time the 0° location passes the pick-up coil, the sampling being accomplished by the sample and hold circuit 100 in response to the sample signal on line 102 from the timing and control circuit 90. For convenience of signal processing, information is converted to digital form by the analog to digital converter 104 and placed into storage 106. Sampling signals are provided on line 102 to cause sampling of the pick-up coil output every complete rotation or 33.3 milliseconds for one complete period of the excitation frequency (20 seconds) so that 600 samples for the 0° location are sampled and stored.

Computation circuit 110 is thereafter operable to compute the average of all the stored samples. If $E'_{i,j}$ represents the output signal of the pick-up coil in any particular instant of time, then the average output signal $\bar{E}$ will be:

$$\bar{E}_i = \frac{\sum_{j=1}^{n} E'_{i,j}}{n} \tag{1}$$

where n equals the number of samples, 600 in the present example, i represents any degree location and j represents any of the 600 samples for that degree location. Under control of the timing and control circuit 90, the computed average from computation circuit 110 is provided to the summing circuit 97, after being converted back to analog form by the digital-to-analog converter 112.

600 samples are obtained during one period of the excitation current so as to compute the average $\bar{E}_i$. The permanent moment signal component of the pick-up coil does not vary with the varying excitation signal as does the crack indicative component. This crack indicative component however, for a particular degree location will always average out to zero since it is averaged over one positive and one negative half cycle of the excitation waveform. With the average signal $\bar{E}_i$ being provided by the digital-to-analog converter 112, summation circuit 97 will provide an output signal $$E_{i,j}=(E'_{i,j}-\bar{E}_i) \tag{2}$$

Thus the output of the summing circuit 97 now represents just the crack (or other anomaly) indicative component $E_{i,j}$ of the pick-up coil output signal. The magnitude of this crack indicative component is for small cracks, miniscule compared to the combined signal and accordingly must be amplified with a much greater gain than was the combined signal when the first 600 samples were taken. Accordingly, the enabling signal on line 94 is removed and gate 116 is enabled by the provision of a signal on line 114 thus allowing a much higher gain amplifier 118 to process the signal. If G1 is the gain of amplifier 98 and G2 the gain of amplifier 118 then depending upon the particular system, G2 may be one or more orders of magnitude greater than G1.

The crack indicative signal provided by amplifier 118 is then sampled over one period of the excitation waveform by means of sample and hold circuit 100 after which the sampled value is converted to digital form and placed into storage 106.

With the signal processing employed in the present invention the noise in the processed signal $E_{i,j}$ is inversely proportional to the square root of the number of samples taken. Therefore the taking of 600 samples at each degree location substantially reduces the noise component of the processed signal. A further reduction in noise is obtained by performing a form of synchronous demodulation on the stored $E_{i,j}$ samples. This demodulation process not only further reduces the noise component but yields in phase and quadrature components for the processed signal with the quadrature component being indicative of conductivity or cracks in the member under test, and the in-phase component being indicative of permeability variations in the steel. The synchronous demodulation is accomplished with the provision of demodulator circuit 120 which receives the stored samples from storage 106 and performs the following summation and multiplication:

$$E_{Ii} = 1/600 \sum_{j=1}^{600} E_{i,j} \sin \omega t_j \quad (3)$$

$$E_{Qi} = 1/600 \sum_{j=1}^{600} E_{i,j} \cos \omega t_j \quad (4)$$

where:
$E_{Ii}$ is the in-phase signal component for the $i^{th}$ degree location
$E_{Qi}$ is the quadrature component for the $i^{th}$ degree location
$\omega = 2\pi f$ where f is the frequency of the excitation current I ($I = I_o \sin \omega t$)
$t_j$ corresponds to the point in time where the $j^{th}$ sample is obtained.

The sine and cosine values are supplied to the demodulator circuit 120 from the sine and cosine look-up tables 122. For the example given, wherein 600 samples are taken during the period of the excitation current, the sine and cosine values in the look-up tables will be given for every 0.6° (360° in one excitation current period divided by 600 samples). As will be subsequently explained, the look-up table 122 may be utilized in the generation of the excitation current.

Figure 9:
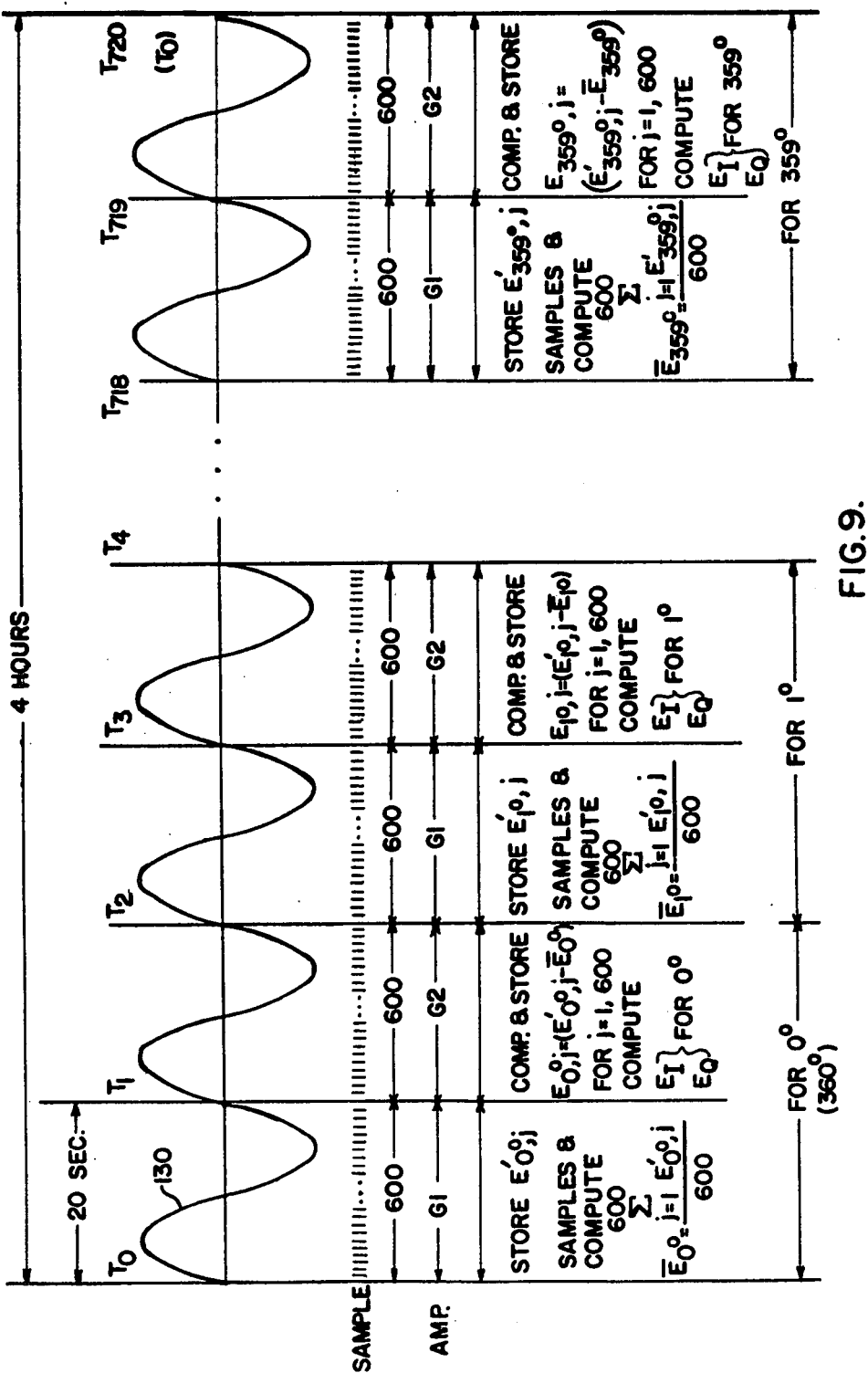
FIG. 9 is a timing chart to illustrate the operation of the circuitry of FIG. 8.

A short summary of the operation of FIG. 8 is presented in FIG. 9 wherein the excitation current is presented as waveform 130 having a frequency of 1/20 Hz and a period of 20 seconds. The time from $T_0$ to $T_2$ is utilized for obtaining values relative to the 0° (or 360°) location of the rotating member under test, the time from $T_2$ to $T_4$ is utilized for obtaining values relative to the 1° location, . . . and the time from $T_{718}$ to $T_{720}$ is utilized for obtaining values relative to the 359° location. In the first time period $T_0$ to $T_1$ 600 samples of the pick-up coil output signal are obtained with the amplifier means set at the relatively lower gain value of G1. The 600 samples are stored and an average $\overline{E}_{0°}$ is computed. From $T_1$ to $T_2$ 600 more samples of the pick-up coil output signal are obtained and from each of which the previously computed average is subtracted, with the amplifier gain setting at the relatively higher value, so as to obtain just the desired crack indicative signal $E_{0°,j}$ for each of the 600 sample points. With a fast signal processing capability the in-phase and quadrature components $E_{I0°}$ and $E_{Q0°}$ for the 0° location may be calculated prior to the beginning of the next cycle at $T_2$ or, alternatively, this calculation of $E_I$ and $E_Q$ for the 0° location may be performed in the subsequent cycle $T_2$ to $T_3$ during which time samples are being taken and stored for the computation of an average signal for the 1° location. This average signal is utilized in the time $T_3$ to $T_4$ to compute the desired crack indicative signal for each of the 600 sample points. This process is continued until the last computations from time $T_{718}$ to $T_{720}$ for the calculation of values relative to the 359° location.

With the example given therefore complete analysis of the rotating member relative to the possible cracks will take a total of four hours. This time however may vary depending upon the computation circuitry utilized. For example, computation of values relative to a particular degree location may take longer than two complete cycles of the excitation current in which case the complete analysis will take longer than four hours. Conversely, during rotation of the member under test, values may be taken for each degree location every 92.59 microseconds for two periods of the excitation current (the first period to obtain averages and the second period to obtain the desired crack indicative signals) thus resulting in a complete analysis in less than one minute.

FIGS. 10A through 10E are waveforms to further illustrate the signal processing of the circuitry of FIG. 8. In FIGS. 10A through 10E angular position $\theta$ of the rotating member is plotted on the X axis, time is plotted on the Y axis and signal magnitude is plotted on the Z axis. The time axis Y is plotted for 20 seconds, one period of the excitation current and sample points along this axis (there would 600 in the present example) correspond to the j values while sample degree locations along the X axis would correspond to the i values.

Figure 10A:
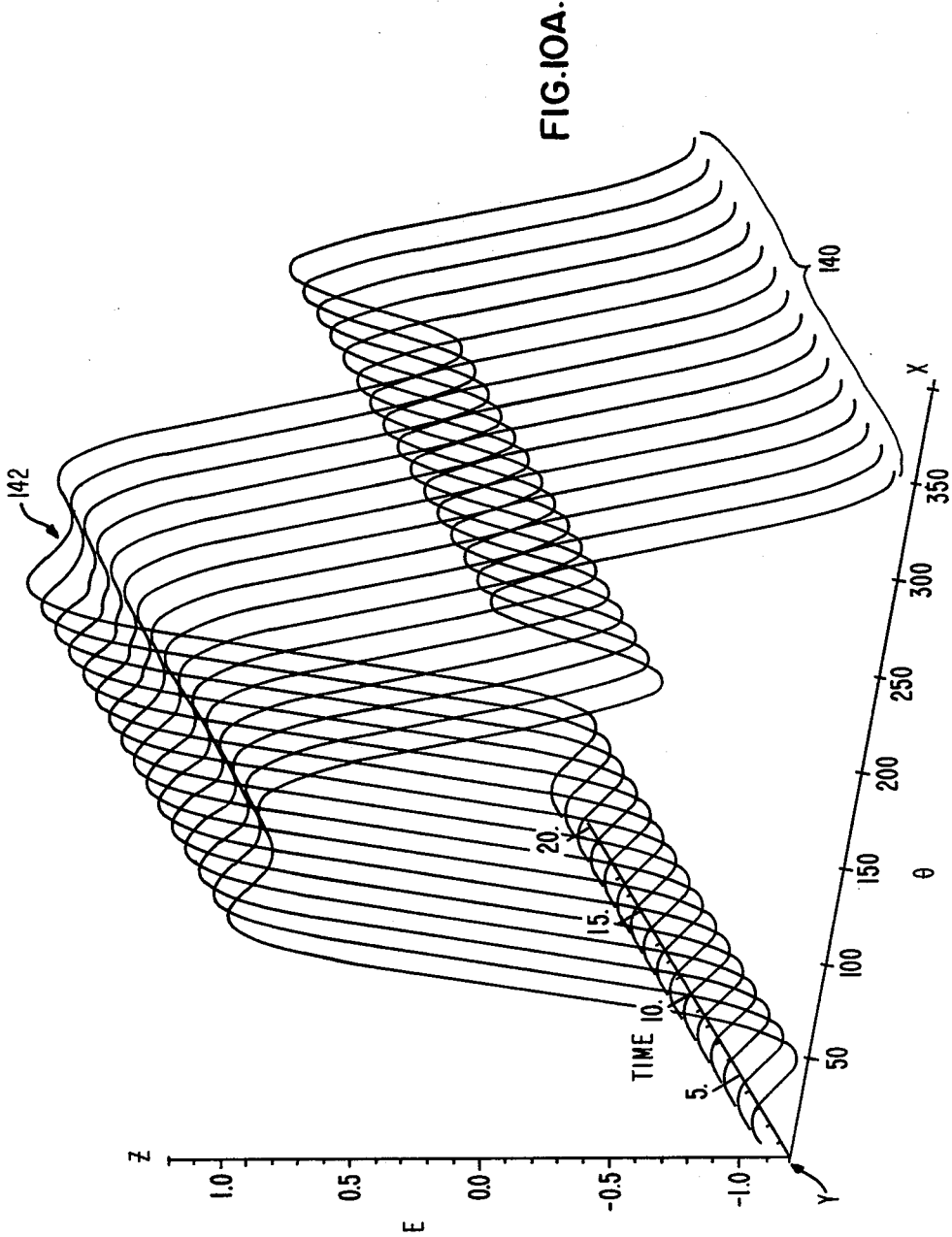
Figure 10B:
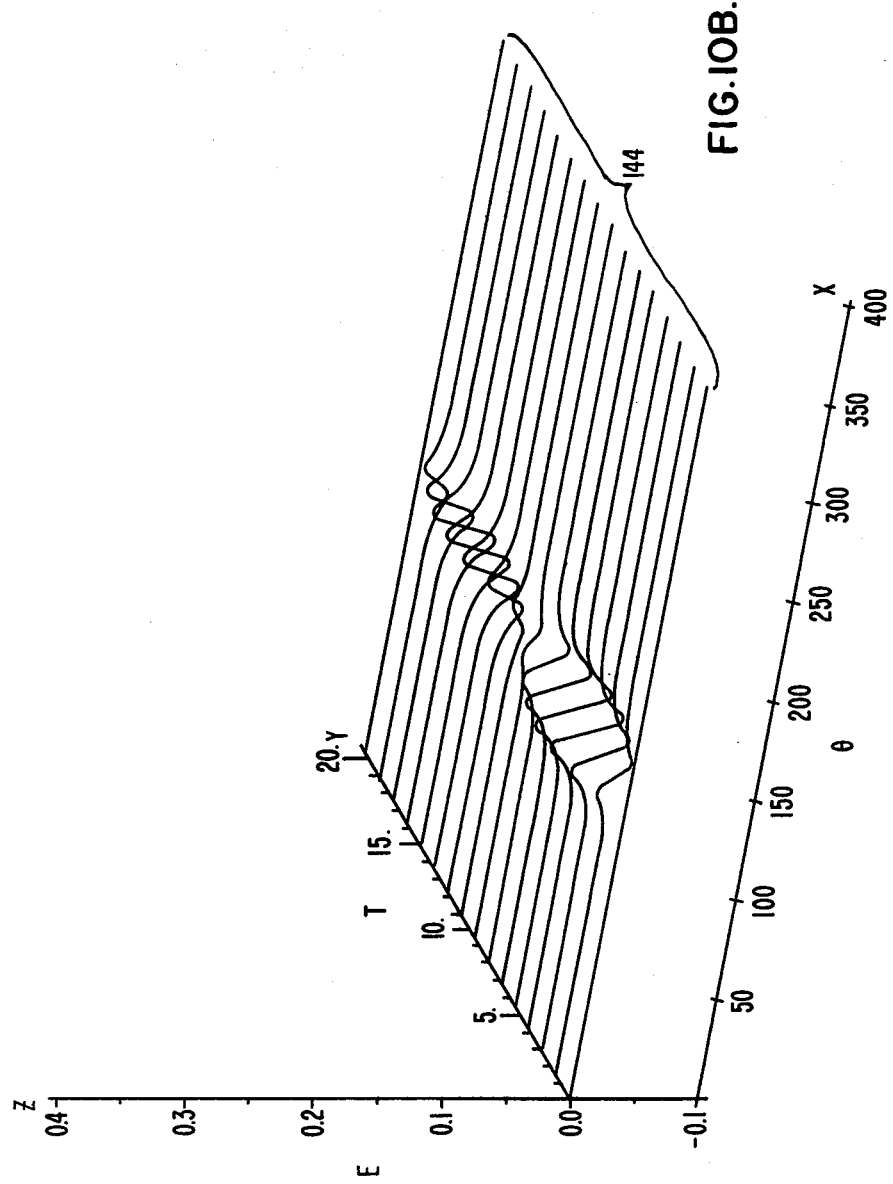

Let it be assumed by way of example that the rotating member under test includes a variety of permanent moments as well as a crack at the 150° location. Waveforms 140 illustrate a plurality of samples of the combined signal taken at 16 different time locations in the period of the excitation current. In actuality in the present example, there would be 600 such waveforms 140 although only 16 are illustrated for clarity. The crack indicative signal superimposed upon the permanent moments signal is almost imperceptable in FIG. 10A and only a hint of it can be seen in the valley 142 following the peak at approximately 125°. The signal processing described herein operates to extract this crack indicative signal by subtracting from the combined signal, an average signal computed for the particular degree locations. The signal resulting from this process is illustrated in FIG. 10B which just shows the crack indicative signals, as represented by waveforms 144, for each of 16 points in the time scale. Although the X and Y coordinates are identical to that illustrated in FIG. 10A, the Z coordinate, signal magnitude, is of a different scale, resulting from the application of the greater gain G2.

Figure 10E:
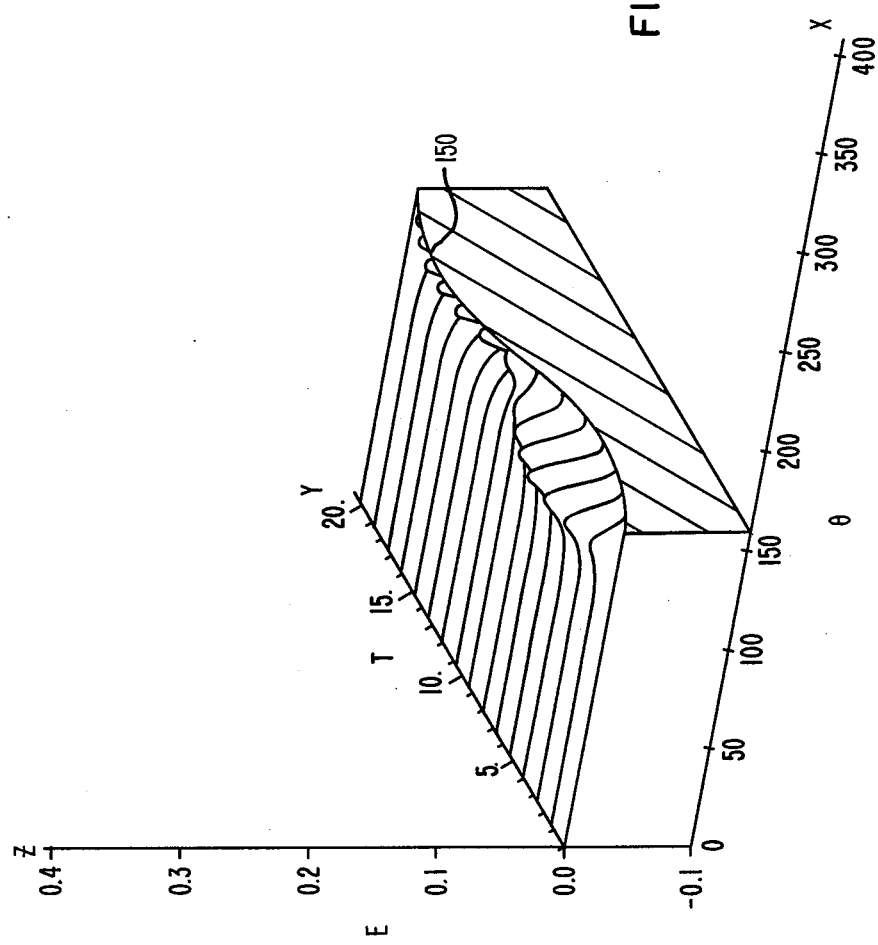

At each degree location in the vicinity of the crack, the magnitude of the waveforms 144 will vary sinusoidally in accordance with the excitation current. By way of example, FIG. 10C illustrates a slice through the waveforms taken at the 140° location, and if the magnitude of all the sampled points are connected, a curve such as 146 will result. It must be remembered that the signal values are changing in two dimensions, that is, in the time dimension related to the changing excitation current (Y axis) and in the angular position dimension of the rotating member (X axis). A cut through the waveforms at the crack location of 150° reveals a straight line 148 as in FIG. 10D while the slice through the waveforms 10° past the crack location or at 160° reveals a curve 150 as illustrated in FIG. 10E. The process of the waveforms 140 rising to a positive maximum as the crack approaches the pick-up coil and then decreasing to a negative maximum corresponds to the waveform 54 of FIG. 4C (where the excitation current is in its positive cycle).

Figure 11:
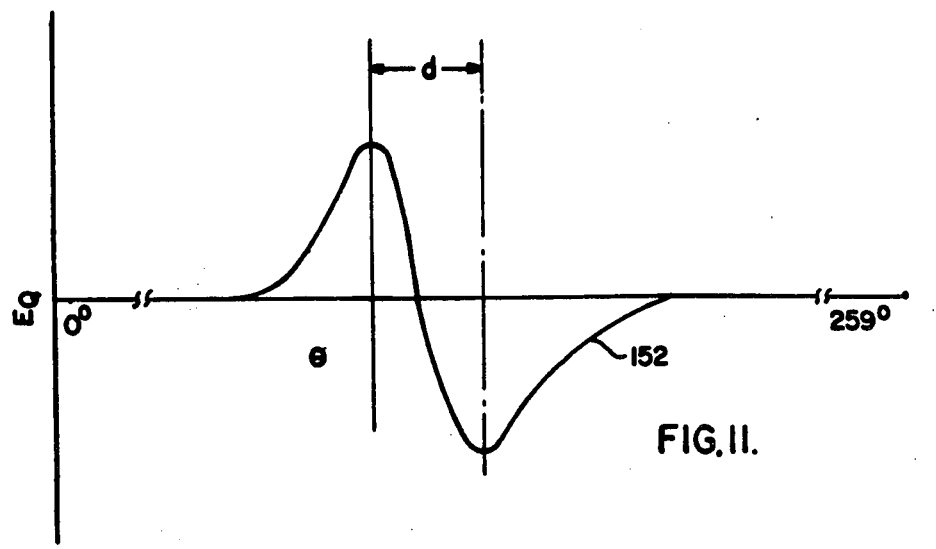
FIG. 11 is an output signal derived by the circuitry of FIG. 8 and indicative of a crack in a rotating member.

As previously described, the individual values for each degree location are further processed by a form of synchronous demodulation to obtain in-phase and quadrature values for each degree location. FIG. 11 illustrates a plot of the quadrature component $E_Q$ obtained as a result of this latter signal processing operation. Rotational angle $\theta$ is plotted on the horizontal axis for 360° and the amplitude of $E_Q$ is plotted on the vertical axis. Such output signal may be recorded, displayed and analyzed by the output circuit 82 of FIG. 6. Basically, the distance d between the positive and negative peaks is indicative of the distance from the center of the pick-up coil to the center of the detected crack. Curve 152 is illustrated as being a continuous curve however it is to be noted that it is actually made up of a plurality of individual values computed for each degree location. A somewhat similar curve (not shown) can be plotted for the in-phase component of the signal to provide an indication of variation of permeability or magnetic hardness.

Figure 12:
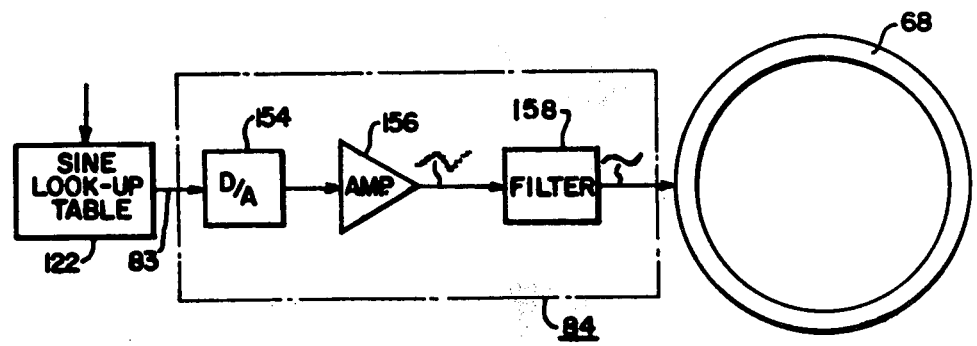
FIG. 12 is a block diagram illustrating the excitation circuitry of FIG. 6 in more detail.

FIG. 12 illustrates the excitation circuit 84 of FIG. 6 in somewhat more detail. The values stored in the sine look-up table 122 are provided to the excitation circuit 84 over line 83 as governed by timing and control circuit 90 (FIG. 8) and the value for each increment (there would be 600 such increments) is converted to an analog form by the digital-to-analog converter 154 and thereafter amplified by amplifier 156. The somewhat stepped signal emanating from the amplifier 156 is smoothed with the provision of filter 158 and thereafter provided to the excitation coil 68.

Figure 13:
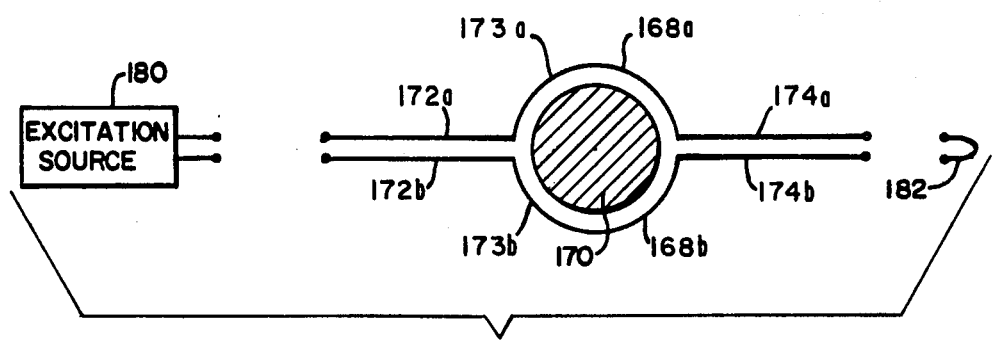
FIG. 13 illustrates a coil arrangement for placement around an operational rotating member.

The examples previously given have illustrated an excitation coil which surrounds a rotating member. The same results may be obtained with a multipart coil the individual parts of which only partially surround the rotating member. This is illustrated in FIG. 13. The energization coil 168 is illustrated as being in two parts 168a and 168b which collectively substantially surround a rotating member 170. The upper portion 168a includes three distinct sections 172a to 174a while the lower part 168b includes similar sections 172b to 174b. If section 172a and 172b are connected to an excitation source 180 and sections 174a and 174b are electrically connected such as by jumper 182 then a circumferential eddy current alternating in direction will be established in the rotating member 170 by virtue of the excitation current in sections 173a and 173b. At any instant of time current in sections 172a and 172b will be equal and opposite and therefore cancel one another, as will currents in sections 174a and 174b. Although only one winding is illustrated, additional windings may be provided with an appropriate amount of additional jumper members. The arrangement illustrated in FIG. 13 is particularly well adapted for use in retrofitting certain rotating machinery where economic or structural circumstances dictate against placing a circular excitation coil around the rotating member.

Figure 14:
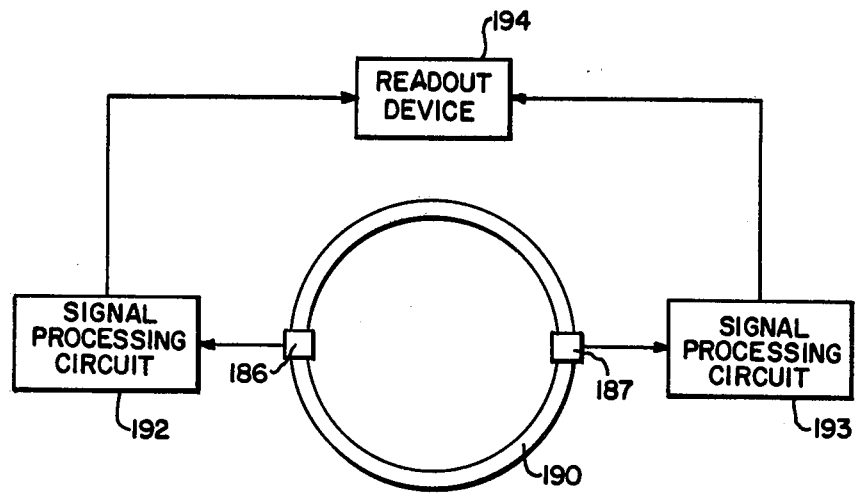
FIG. 14 illustrates a plural coil arrangement for reducing testing time.

The embodiment of the invention thus far described utilizes a single pick-up coil in conjunction with the excitation coil. A faster analysis may be obtained with the use of multiple pick-up coils such as illustrated in FIG. 14. Two pick-up coils 186 and 187 are illustrated in conjunction with an excitation coil 190 which would be placed around the member to be tested. Each of the pick-up coils 186 and 187 provide their output signals to respective signal-processing circuits 192 and 193, each operable as previously described with respect to FIG. 8 for computing respective $E_I$ and $E_Q$ signals and providing them to a readout device 194.

Although only two pick-up coils 186 and 187 are illustrated, it is to be understood that additional coils may be supplied in conjunction with signal-processing circuitry to further reduce the analysis time. In the embodiment of FIG. 14 the pick-up coils are diametrically opposed such that pick-up coil 186 and associated signal-processing circuitry 192 may process signals related to the first 180° of rotation whereas pick-up coil 187 in conjunction with signal-processing circuitry 193 would process the second 180°.

An arrangement of plural pick-up coils may also be utilized to reduce the effects of extraneous noise. For example, in FIG. 15 numeral 200 represents a device which produces an external magnetic field 202 which represents an unwanted noise source to the detection apparatus 204. That is, the magnetic field 202 may vary the output signal of a pick-up coil, such variation therefor being completely independent of any anomaly in the member under test.

Figure 16:
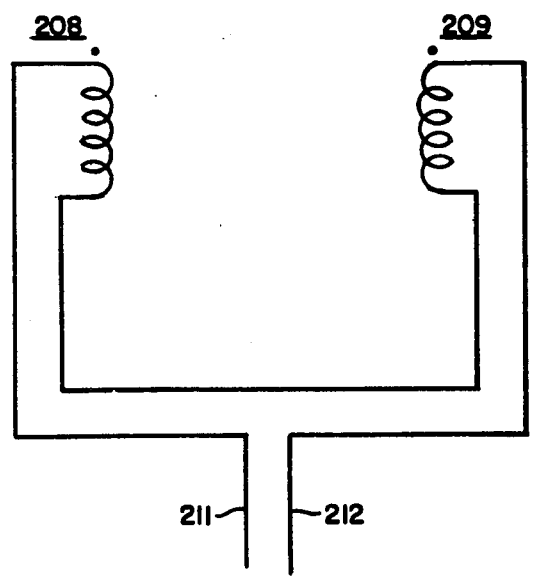
FIG. 16 further illustrates the connection of the pick-up coils of FIG. 15.
Figure 15:
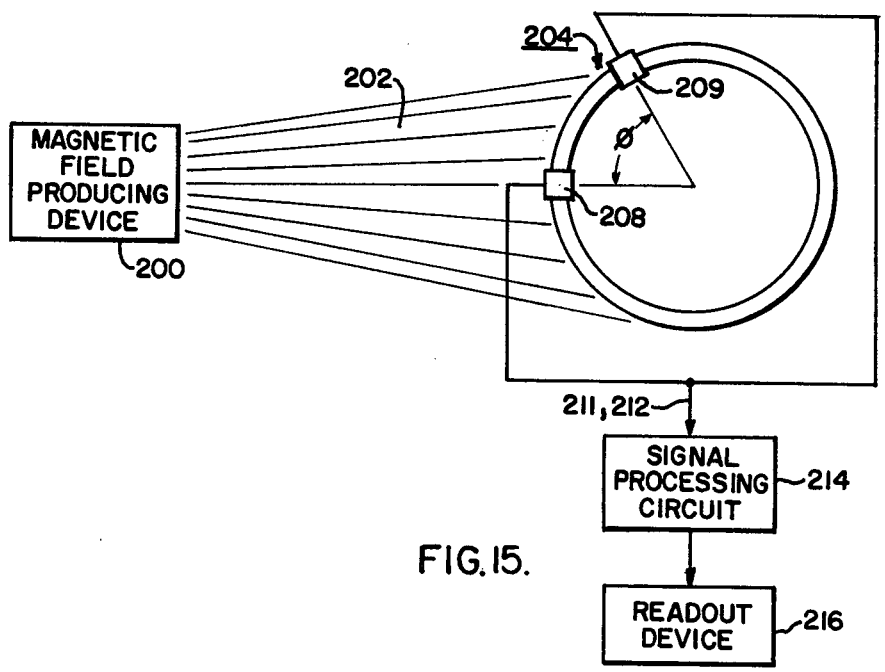
FIG. 15 illustrates a plural coil arrangement for reducing the effects of extraneous magnetic noise.

In order to reduce, if not eliminate, the undesired effects of this external magnetic field, the arrangement of FIG. 15 includes first and second pick-up coils 208 and 209 connected in signal opposition to one another, as in FIG. 16, so as to provide, on lines 211 and 212 a resultant output signal to the signal-processing circuit 214 operable as previously described to generate output signals to the readout 216.

Any crack located in the member under test will generate two indications thereof, one due to the crack passing pick-up coil 208 and the other due to the crack passing pick-up coil 209 angularly displaced from pick-up coil 208 by $\phi$ degrees. The final readout, accordingly, will indicate an anomaly at a certain angular location and a second one at an angular location $\phi$ degrees spaced from the first indication. The magnetic field 202, however, simultaneously affects both pick-up coils 208 and 209 and, accordingly, due to their connection as illustrated in FIG. 16 the same signal generated in both pick-up coils due to the disturbance will cancel out.

Although the invention has been described with a certain degree of particularity it is evident that many variations are possible. For example, FIG. 8 illustrates a signal processing arrangement which utilizes digital signals. It is evident that the signal processing can be accomplished with purely analog circuitry or alternatively the entire signal processing function of FIG. 8 can be accomplished with a single digital computer.

Furthermore, the operation of the circuitry was explained with respect to taking 600 samples in one period of the excitation current. The sampling of course can be for N periods of the excitation current and the sampling can be at other than every single degree location.

What is claimed is:

1. Apparatus for detecting anomalies in an electrically conducting rotating member comprising:
   (A) current conducting means contiguous said rotating member operable to establish a circumferential alternating eddy current therein, and a corresponding external magnetic field, as said member rotates;
   (B) means for providing said current conducting means with an AC excitation current having a frequency f;

(C) the period of said excitation current being orders of magnitude greater than the period of rotation of said rotating member;

(D) sensing means contiguous said rotating member for detecting any changes in said magnetic field caused by said anomalies and operable to provide an output signal indicative thereof;

(E) signal processing means operable in response to said output signal to provide an indication of anomaly and anomaly location within said rotating member.

2. Apparatus according to claim 1 wherein:
(A) said frequency f is a fraction of a Hertz.

3. Apparatus according to claim 1 wherein:
(A) said output signal of said sensing means is periodically sampled by said signal processing means at least several hundred times during said period of said excitation current.

4. Apparatus according to claim 1 wherein:
(A) said output signal of said sensing means is sampled at least once during each complete rotation of said rotating member.

5. Apparatus according to claim 1 wherein:
(A) said current conducting means is a coil which uninterruptedly surrounds said rotating member.

6. Apparatus according to claim 5 wherein:
(A) said sensing means is a pick-up coil disposed adjacent said current conducting means.

7. Apparatus according to claim 1 wherein:
(A) said current conducting means is a multipart coil each part of which does not surround said rotating member but all the parts of which collectively substantially surround said rotating member.

8. Apparatus according to claim 1 wherein:
(A) said signal processing means is operable to eliminate the undesired effects that any residual magnetism of said rotating member may have on said output signal.

9. Apparatus according to claim 8 wherein:
(A) said signal processing means is operable to sample said output signal of said sensing means a predetermined number of times, for each of a predetermined number of degree locations around said rotating member, to compute in a first time period, for each said degree location, an average value of said output signal ($\bar{E}_i$) and to subtract, in a subsequent time period, said average value from said output signal to obtain an anomaly signal.

10. Apparatus according to claim 9 wherein:
(A) said output signal is sampled a predetermined number of times for each of 360 degree locations around said rotating member.

11. Apparatus according to claim 9 wherein:
(A) said signal processing means is operable to further process said anomaly signal to obtain in-phase and quadrature components thereof.

12. Apparatus according to claim 1 wherein:
(A) said signal processing means controls the generation of said AC excitation current.

13. Apparatus according to claim 1 wherein:
(A) said sensing means includes a plurality of pick-up coils angularly disposed about said rotating member.

14. Apparatus according to claim 13 which includes:
(A) a plurality of signal-processing means each connected to a respective one of said pick-up coils and each operable in response to the output signal provided by the respective pick-up coils to provide an indication of anomaly and anomaly location within said rotating member.

15. Apparatus according to claim 13 wherein:
(A) said pick-up coils are electrically connected in signal opposition so as to tend to cancel any signals caused by an external magnetic field acting simultaneously on said pick-up coils.

16. A method of detecting anomalies in an electrically conducting rotating member comprising the steps of:
(A) establishing, in said member as it rotates, a circumferential alternating eddy current having a period which is orders of magnitude greater than the period of rotation of said rotating member;
(B) detecting the resultant magnetic field due to said eddy current and providing a signal indicative thereof; and
(C) processing said signal to obtain an indication of anomaly and anomaly location within said rotating member.

17. A method according to claim 16 wherein:
(A) said signal is processed to eliminate the effects of any residual magnetism of said rotating member.

18. A method according to claim 16 wherein:
(A) said signal is processed to obtain a first component indicative of permeability and a second component indicative of conductivity.

19. A method according to claim 16 wherein:
(A) said signal is sampled at least hundreds of times in one period of said alternating eddy current.

20. A method according to claim 18 which includes the step of:
(A) providing a graphic printout of at least one of said component indications.

* * * * *